US011400692B2

(12) United States Patent
Bonekamp et al.

(10) Patent No.: US 11,400,692 B2
(45) Date of Patent: Aug. 2, 2022

(54) ODOR-MANAGED OSTOMY FILM

(71) Applicant: Dow Global Technologies LLC, Midland, MI (US)

(72) Inventors: Jeffrey E. Bonekamp, Midland, MI (US); Ronald Wevers, Terneuzen (NL); Scott T. Matteucci, Midland, MI (US); Arkady L. Krasovskiy, Lake Jackson, TX (US); Kefu Sun, Lake Jackson, TX (US); Keran Lu, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 23 days.

(21) Appl. No.: 17/270,554

(22) PCT Filed: Aug. 23, 2019

(86) PCT No.: PCT/US2019/047862
§ 371 (c)(1),
(2) Date: Feb. 23, 2021

(87) PCT Pub. No.: WO2020/046736
PCT Pub. Date: Mar. 5, 2020

(65) Prior Publication Data
US 2021/0187920 A1 Jun. 24, 2021

Related U.S. Application Data

(60) Provisional application No. 62/725,391, filed on Aug. 31, 2018.

(51) Int. Cl.
*B32B 27/08* (2006.01)
*A61F 5/441* (2006.01)
*B32B 1/00* (2006.01)
*B32B 25/08* (2006.01)
*B32B 25/14* (2006.01)
*B32B 25/16* (2006.01)
*B32B 27/20* (2006.01)
*B32B 27/30* (2006.01)
*B32B 27/32* (2006.01)
*B32B 27/34* (2006.01)
*B32B 27/36* (2006.01)

(52) U.S. Cl.
CPC .............. *B32B 27/08* (2013.01); *A61F 5/441* (2013.01); *B32B 1/00* (2013.01); *B32B 25/08* (2013.01); *B32B 25/14* (2013.01); *B32B 25/16* (2013.01); *B32B 27/20* (2013.01); *B32B 27/304* (2013.01); *B32B 27/306* (2013.01); *B32B 27/308* (2013.01); *B32B 27/32* (2013.01); *B32B 27/327* (2013.01); *B32B 27/34* (2013.01); *B32B 27/36* (2013.01); *B32B 2250/04* (2013.01); *B32B 2250/24* (2013.01); *B32B 2264/1025* (2020.08); *B32B 2264/12* (2013.01); *B32B 2307/7244* (2013.01); *B32B 2307/7246* (2013.01); *B32B 2307/7248* (2013.01); *B32B 2439/80* (2013.01); *B32B 2535/00* (2013.01)

(58) Field of Classification Search
CPC . B32B 27/08; B32B 2535/00; B32B 2439/80; B32B 2307/7248; B32B 2307/7246; B32B 2307/7244; B32B 2250/24; B32B 2250/04; B32B 2264/1025; B32B 27/36; B32B 27/34; B32B 27/327; B32B 27/32; B32B 27/308; B32B 27/306; B32B 27/304; B32B 27/20; B32B 25/16; B32B 25/14; B32B 25/08; B32B 1/00; A61F 5/441
See application file for complete search history.

(56) References Cited

U.S. PATENT DOCUMENTS

| | | |
|---|---|---|
| 4,757,099 A | 7/1988 | Hoshino et al. |
| 5,677,383 A | 10/1997 | Chum et al. |
| 6,111,023 A | 8/2000 | Chum et al. |
| 6,258,423 B1 | 7/2001 | Giori |
| 6,448,335 B1 | 9/2002 | Braga et al. |
| 6,455,161 B1 | 9/2002 | Regnier et al. |
| 6,521,553 B1 | 2/2003 | Tabata et al. |
| 6,984,695 B2 | 1/2006 | Brown et al. |
| 9,108,380 B2 | 8/2015 | Binger et al. |
| 2005/0287318 A1 | 12/2005 | Speer et al. |
| 2007/0210281 A1 | 9/2007 | Speer et al. |
| 2009/0006770 A1 | 1/2009 | Blumrich et al. |
| 2010/0300905 A1 | 12/2010 | Speer et al. |
| 2013/0096521 A1 | 4/2013 | Bekele |
| 2013/0164467 A1 | 6/2013 | Speer et al. |
| 2018/0362232 A1 | 12/2018 | Spigaroli et al. |
| 2020/0039173 A1 | 2/2020 | Brebion et al. |

FOREIGN PATENT DOCUMENTS

| | | |
|---|---|---|
| JP | 2000225180 A | 8/2000 |
| JP | 2018086127 A | 6/2018 |
| WO | 95/20624 A1 | 8/1995 |

*Primary Examiner* — Ellen S Hock
(74) *Attorney, Agent, or Firm* — Quarles & Brady LLP

(57) ABSTRACT

The present disclosure provides a film. In an embodiment, a multilayer film is provided and includes (A) a seal layer, (B) a barrier layer, and (C) an odor control layer. The odor control layer includes an odor control composition containing (A) from 85 wt % to 99.5 wt % of an olefin-based polymer and (B) from 15 wt % to 0.5 wt % of an odor suppressant. The odor suppressant includes a blend of: (i) an ionomer, (ii) particles of zinc oxide, and (iii) particles of copper oxide. The composition has a methyl mercaptan odor suppression value of greater than 45% as measured in accordance with ASTM D5504-12.

15 Claims, No Drawings

ODOR-MANAGED OSTOMY FILM

BACKGROUND

Polyvinylidene chloride "PVDC" is a known barrier material found in many odor suppression applications such as ostomy films, for example. PVDC, however, has several shortcomings. Films constructed with PVDC barrier layers oftentimes exhibit high noise during production, creating a health hazard to operators. PVDC also contains chlorine, a known environmental hazard.

Efforts at down-gauging PVDC (or eliminating PVDC altogether) in barrier films have met with limited success. Thinner PVDC barrier layers come with reduced ability to suppress odor. Chlorine-free barrier layers typically do not provide the same odor suppression ability as a comparable film with a PVDC barrier layer.

It is also known that odor absorbers or deodorants can be added to polymeric film in an effort to suppress odor. Metal oxides such as zinc oxide (ZnO) particles, and zinc salts in particular, are known to consume many odor-generating molecules such as $H_2S$ and mercaptans. All other factors being equal, it is known that ZnO concentration and odor suppression are directly related—i.e., as ZnO concentration increases in a given olefin-based polymer article, the effectiveness of odor suppression also increases.

Although odor suppression increases as metal oxide (ZnO in particular) increases, limits do exist for the amount of ZnO that can be effectively incorporated into olefin-based polymer films. High loading of ZnO particles in polymeric films increases extrusion die lip buildup, thereby causing film defects. High loading of ZnO particles also increases haze, resulting in degradation of olefin-based polymer film transparency and/or degradation in film color. High loading of ZnO particles also deleteriously impacts mechanical properties such as impact strength and film tear strength. Processing parameters and end-use mechanical requirements thereby impose practical limits to the load of odor absorbers, such as ZnO particles, into olefin-based polymer compositions.

A need therefore exists for a multilayer film, having improved odor-suppressing capabilities that overcome the limitations of high loading of ZnO particles. A need further exists for a multilayer film (such as an ostomy film) with suitable processability and suitable mechanical properties which reduces, or eliminates, the presence of halogen (chlorine) in the film.

SUMMARY

The present disclosure provides a film. In an embodiment, a multilayer film is provided and includes (A) a seal layer, (B) a barrier layer, and (C) an odor control layer. The odor control layer includes an odor control composition containing (A) from 85 wt % to 99.5 wt % of at least one olefin-based polymer and (B) from 15 wt % to 0.5 wt % of an odor suppressant. The odor suppressant includes a blend of: (i) an ionomer, (ii) particles of zinc oxide, and (iii) particles of copper oxide. The composition has a methyl mercaptan odor suppression value of greater than 45% as measured in accordance with ASTM D5504-12.

The present disclosure provides a bag. In an embodiment, an ostomy bag is provided and includes a first multilayer film and a second multilayer film. Each multilayer film includes (A) a seal layer, a barrier layer, and (C) an odor control layer. The odor control layer includes a composition containing (A) from 85 wt % to 99.5 wt % of an olefin-based polymer and (B) from 15 wt % to 0.5 wt % of an odor suppressant. The odor suppressant includes a blend of: (i) an ionomer, (ii) particles of zinc oxide, and (iii) particles of copper oxide. The composition has a methyl mercaptan odor suppression value of greater than 45% as measured in accordance with ASTM D5504-12. The first multilayer film and the second multilayer film are arranged such that the seal layers oppose each other and the second multilayer film is superimposed on the first multilayer film to form a common peripheral edge. The first multilayer film and the second multilayer film are sealed along the common peripheral edge. The first multilayer film includes a first opening, with a ring adhered to the first opening.

Definitions

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2, or 3 to 5, or 6, or 7), any subrange between any two explicit values is included (e.g., the range 1-7 above includes subranges of 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

An "agglomerate" is a plurality of individual fine solid particles clumped or otherwise together forming a single mass.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

An "ethylene-based polymer" is a polymer that contains more than 50 weight percent (wt %) polymerized ethylene monomer (based on the total amount of polymerizable monomers) and, optionally, may contain at least one comonomer. Ethylene-based polymer includes ethylene homopolymer, and ethylene copolymer (meaning units derived from ethylene and one or more comonomers). The terms "ethylene-based polymer" and "polyethylene" may be used interchangeably. Non-limiting examples of ethylene-based polymer (polyethylene) include low density polyethylene (LDPE) and linear polyethylene. Non-limiting examples of linear polyethylene include linear low density polyethylene (LLDPE), ultra-low density polyethylene (ULDPE), very low density polyethylene (VLDPE), multi-component ethylene-based copolymer (EPE), ethylene/α-olefin multi-block copolymers (also known as olefin block copolymer (OBC)), substantially linear, or linear, plastomers/elastomers, and high density polyethylene (HDPE). Generally, polyethylene may be produced in gas-phase, fluidized bed reactors, liquid phase slurry process reactors, or liquid phase solution process reactors, using a heterogeneous catalyst system, such as Ziegler-Natta catalyst, a homogeneous catalyst system, comprising Group 4 transition metals and ligand structures such as metallocene, non-metallocene metal-centered, heteroaryl, heterovalent aryloxyether, phosphinimine, and others. Combinations of heterogeneous and/or homogeneous catalysts also may be used in either single reactor or dual reactor configurations.

"Ethylene plastomers/elastomers" are substantially linear, or linear, ethylene/α-olefin copolymers containing homogeneous short-chain branching distribution comprising units derived from ethylene and units derived from at least one C3-C10 α-olefin comonomer. Ethylene plastomers/elastomers have a density from 0.870 g/cc to 0.917 g/cc. Non-limiting examples of ethylene plastomers/elastomers include AFFINITY™ plastomers and elastomers (available from The Dow Chemical Company), EXACT™ Plastomers (available from ExxonMobil Chemical), Tafmer™ (available from Mitsui), Nexlene™ (available from SK Chemicals Co.), and Lucene™ (available LG Chem Ltd.).

"High density polyethylene" (or "HDPE") is an ethylene homopolymer or an ethylene/α-olefin copolymer with at least one C4-C10 α-olefin comonomer, or C4-C8 α-olefin comonomer and a density from 0.940 g/cc, or 0.945 g/cc, or 0.950 g/cc, 0.953 g/cc to 0.955 g/cc, or 0.960 g/cc, or 0.965 g/cc, or 0.970 g/cc, or 0.975 g/cc, or 0.980 g/cc. The HDPE can be a monomodal copolymer or a multimodal copolymer. A "monomodal ethylene copolymer" is an ethylene/C4-C10 α-olefin copolymer that has one distinct peak in a gel permeation chromatography (GPC) showing the molecular weight distribution. A "multimodal ethylene copolymer" is an ethylene/C4-C10 α-olefin copolymer that has at least two distinct peaks in a GPC showing the molecular weight distribution. Multimodal includes copolymer having two peaks (bimodal) as well as copolymer having more than two peaks. Non-limiting examples of HDPE include DOW™ High Density Polyethylene (HDPE) Resins (available from The Dow Chemical Company), ELITE™ Enhanced Polyethylene Resins (available from The Dow Chemical Company), CONTINUUM™ Bimodal Polyethylene Resins (available from The Dow Chemical Company), LUPOLEN™ (available from LyondellBasell), as well as HDPE products from Borealis, Ineos, and ExxonMobil.

An "interpolymer" is a polymer prepared by the polymerization of at least two different monomers. This generic term includes copolymers, usually employed to refer to polymers prepared from two different monomers, and polymers prepared from more than two different monomers, e.g., terpolymers, tetrapolymers, etc.

"Linear low density polyethylene" (or "LLDPE") is a linear ethylene/α-olefin copolymer containing heterogeneous short-chain branching distribution comprising units derived from ethylene and units derived from at least one C3-C10 α-olefin, or C4-C8 α-olefin, comonomer. LLDPE is characterized by little, if any, long chain branching, in contrast to conventional LDPE. LLDPE has a density from 0.910 g/cc to less than 0.940 g/cc. Non-limiting examples of LLDPE include TUFLIN™ linear low density polyethylene resins (available from The Dow Chemical Company), DOWLEX™ polyethylene resins, e.g. DOWLEX™ 2247G (available from the Dow Chemical Company), and MARLEX™ polyethylene (available from Chevron Phillips).

"Low density polyethylene" (or "LDPE") consists of ethylene homopolymer, or ethylene/α-olefin copolymer comprising at least one C3-C10 α-olefin, or C4-C8 α-olefin, that has a density from 0.915 g/cc to less than 0.940 g/cc and contains long chain branching with broad MWD. LDPE is typically produced by way of high pressure free radical polymerization (tubular reactor or autoclave with free radical initiator). Non-limiting examples of LDPE include MarFlex™ (Chevron Phillips), LUPOLEN™ (LyondellBasell), as well as LDPE products from Borealis, Ineos, ExxonMobil, and others.

"Multi-component ethylene-based copolymer" (or "EPE") comprises units derived from ethylene and units derived from at least one C3-C10 α-olefin, or C4-C8 α-olefin, comonomer, such as described in patent references U.S. Pat. Nos. 6,111,023; 5,677,383; and 6,984,695. EPE resins have a density from 0.905 g/cc to 0.962 g/cc. Non-limiting examples of EPE resins include ELITE™ enhanced polyethylene (available from The Dow Chemical Company), ELITE AT™ advanced technology resins (available from The Dow Chemical Company), SURPASS™ Polyethylene (PE) Resins (available from Nova Chemicals), and SMART™ (available from SK Chemicals Co.).

An "olefin-based polymer" or "polyolefin" is a polymer that contains more than 50 weight percent polymerized olefin monomer (based on total amount of polymerizable monomers), and optionally, may contain at least one comonomer. Non-limiting examples of an olefin-based polymer include ethylene-based polymer or propylene-based polymer.

A "polymer" is a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymer, e.g., random, block, etc. The terms "ethylene/α-olefin polymer" and "propylene/α-olefin polymer" are indicative of copolymer as described above prepared from polymerizing ethylene or propylene respectively and one or more additional, polymerizable α-olefin monomer. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to has being based on "units" that are the polymerized form of a corresponding monomer.

A "propylene-based polymer" is a polymer that contains more than 50 weight percent polymerized propylene monomer (based on the total amount of polymerizable monomers) and, optionally, may contain at least one comonomer. Propylene-based polymer includes propylene homopolymer, and propylene copolymer (meaning units derived from propylene and one or more comonomers). The terms "propylene-based polymer" and "polypropylene" may be used interchangeably. Non-limiting examples of suitable propylene copolymer include propylene impact copolymer and propylene random copolymer.

"Ultra-low density polyethylene" (or "ULDPE") and "very low density polyethylene" (or "VLDPE") each is a linear ethylene/α-olefin copolymer containing heterogeneous short-chain branching distribution comprising units derived from ethylene and units derived from at least one C3-C10 α-olefin comonomer. ULDPE and VLDPE each has a density from 0.885 g/cc to 0.915 g/cc. Non-limiting examples of ULDPE and VLDPE include ATTANE™ ultra low density polyethylene resins (available from The Dow Chemical Company) and FLEXOMER™ very low density polyethylene resins (available from The Dow Chemical Company).

Test Methods

D10, D50, and D90 particle size is measured using a Coulter LS 230 Laser Light Scattering Particle Sizer, available from Coulter Corporation. D10 particle size is the particle diameter at which 10% of the powder's mass is composed of particles with a diameter less than this value. D50 particle size is the particle diameter at which 50% of the powder's mass is composed of particles with a diameter less than this value and 50% of the powder's mass is composed of particles with a diameter greater than said value. D90 particle size is the particle diameter at which 90% of the powder's mass is composed of particles with a diameter less than this value. Mean volume average particle size is measured using a Coulter LS 230 Laser Light Scattering Particle Sizer, available from Coulter Corporation. Particle size distribution is calculated in accordance with Equation A:

$$\text{Particle size distribution} = \frac{(D90 - D10)}{D50}. \quad \text{Equation A}$$

Dart impact strength is measured in accordance with ASTM D1709, with results reported in grams (g).

Density is measured in accordance with ASTM D792, Method B. The result is recorded in grams per cubic centimeter (g/cc).

Differential Scanning Calorimetry (DSC). Differential Scanning Calorimetry (DSC) can be used to measure the melting, crystallization, and glass transition behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (about 25° C.). A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate and held isothermal at −40° C. for 3 minutes. The sample is then heated to 180° C. (this is the "second heat" ramp) at a 10° C./minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are extrapolated onset of melting, Tm, and extrapolated onset of crystallization, Tc. Heat of fusion (Hf) (in Joules per gram), and the calculated % crystallinity for polyethylene samples using the following Equation: % Crystallinity=((Hf)/292 J/g)×100. Glass transition temperature, Tg, is determined from the DSC heating curve where half the sample has gained the liquid heat capacity as described in Bernhard Wunderlich, *The Basis of Thermal Analysis, in Thermal Characterization of Polymeric Materials* 92, 278-279 (Edith A. Turi ed., 2d ed. 1997). Baselines are drawn from below and above the glass transition region and extrapolated through the Tg region. The temperature at which the sample heat capacity is half-way between these baselines is the Tg.

Elmendorf tear (or tear) is measured in accordance with ASTM D1922-15, machine direction (MD), with results reported in grams-force (gf).

Melt flow rate (MFR) in g/10 min is measured in accordance with ASTM D1238 (230° C./2.16 kg).

Melt index (MI) (I2) in g/10 min is measured in accordance with ASTM D1238 (190° C./2.16 kg).

Odor Suppression/Odor Suppression Value.

Odor suppression is the ability of a composition to neutralize, or otherwise reduce, the amount of volatile sulfur-containing compounds. In the present disclosure, the odor suppression for methyl mercaptan is measured with gas chromatography equipped with an Agilent Sulfur Chemiluminescence Detector (GC-SCD) in accordance with ASTM D5504-12. A control sample is prepared by placing a film formed from DOWLEX™ 2085G, ethylene/octene LLDPE, into a Tedlar® bag (polyvinyl fluoride). The Tedlar® bag for the control is subsequently filled with 900 mL of helium gas and known amounts of methyl mercaptan and the Tedlar® bag is closed. Test samples are prepared by placing a film formed from respective test compositions, each test film placed into a respective Tedlar® bag. Each Tedlar® bag is subsequently filled with 900 mL of helium gas and known amounts of methyl mercaptan, and the Tedlar® bag is closed. Samples are injected onto the GC-SCD at predetermined time intervals from each bag in order to evaluate odor suppression capability.

The reference samples and test samples were analyzed after two days. The reference sample was used as the calibration standard to calculate the methyl mercaptan concentration of each test sample.

A. Sample Preparation

The control sample and each test sample containing 5 ppmv methyl mercaptan were prepared in SKC 1 L sample bag (SKC Tedlar® Sample Bag, 1 Liter, Cat No. 232-01). A reference sample without a film was prepared in a Tedlar® bag as the calibration standard.
1. Cut 1.0 g of film into strips (approximately 1 cm×30 cm).
2. Unscrew the valve from the sample bag, insert the film strips into the bag through the valve opening with the handle of cotton tipped applicator, and install the valve back to the sample bag, squeeze air out of bag before tightening the valve to seal the bag.
3. Fill the bag with 0.90 L of helium gas (AirGas, Ultra Grade Helium)
4. Inject 50 mL of containing 100 ppmv methyl mercaptan, into the bag using a gas-tight glass syringe.

The Odor Suppression Value test can also be done for other odorants, including ethyl mercaptan, propyl mercaptan, and butyl mercaptan.

B. GC-SCD Conditions
1. Gas chromatograph: Agilent Model 7890 with a split/splitless injection port, available from Agilent Technologies, 2850 Centerville Road, Wilmington, Del. 19808.
2. Detector: Agilent Sulfur Chemiluminescence (SCD), Model G6644A.
3. Chromatography data system: Agilent OpenLAB software.
4. Columns: Agilent J&W DB-1 30 m×0.32 mm ID, 5 μm film thickness.
5. Carrier Gas: Hydrogen, constant flow mode, 2.0 mL/min.
6. Inlet: Split, temperature: 250° C., split ratio: 100:1.
7. Injection volume: 500 μL by Valco Six Port Valve, Loop Size: 500 μL.
8. Oven Temperature: 30° C. hold for 1 minute, 15° C./min to 140° C., hold for 1 minutes.
9. SCD Detector Conditions:
Temperature: 250° C.
Hydrogen Flow: 38.3 mL/min.
Oxidizer Flow: 59.9 sccm.
Pressure: 400 Torr.

An odor suppression value (OSV) is the removal % of methyl mercaptan calculated by the following equation:

$$OSV = \frac{\text{Concentration of Reference Sample} - \text{Concentration of Test Sample}}{\text{Concentration of Reference Sample}} \times 100$$

$$= \frac{\text{Peak Area of Reference Sample} - \text{Peak Area of Test Sample}}{\text{Peak Area of Reference Sample}} \times 100$$

The Peak Area is the response of GC-SCD.

A non-limiting example of OSV calculation is provided. At two days the GC-SCD peak area of methylmercaptan in the reference sample is 28240298, whereas the GC-SCD peak area of methyl mercaptan in the test sample IE 1 is 5667327 (unit is pA*s in Agilent OpenLAB software). The odor suppression value for the test sample IE 1 is (((28240298−5667327)/28240298)*100=80. As shown in the equation of OSV, both concentration of methyl mercaptan and GC-SCD Peak Area of methyl mercaptan can be used to calculate OSV.

Porosity and Surface Area. Brunauer-Emmett-Teller (BET) porosity and surface area analysis are performed using a Micromeritics Accelerated Surface Area & Porosimetry instrument (ASAP 2420). The sample is out-gassed at 105° C. while under vacuum prior to analysis.

The ASAP 2420 instrument employs a static (volumetric) method of dosing samples and measures the quantity of gas that can be physically adsorbed (physisorbed) on a solid at liquid nitrogen temperature. For the multi-point BET measurement the volume of nitrogen uptake is measured at pre-selected relative pressure points at constant temperature. The relative pressure is the ratio of the applied nitrogen pressure to the vapor pressure of nitrogen at the analysis temperature of 77 Kelvin (K). Results for porosity are reported in cubic meters per gram, or $m^3/g$. Results for surface area are reported in square meters per gram, or $m^2/g$.

Zinc/copper—total amount. The total amount of zinc and/or copper present in a composition is determined with x-ray fluorescence spectrometry (XRS), in accordance with ASTM D6247. Results are reported in parts per million, or ppm.

DETAILED DESCRIPTION

The present disclosure provides a multilayer film. In an embodiment, a multilayer film is provided and includes (A) a seal layer, (B) a barrier layer, and (C) an odor control layer including a composition that is an odor control composition. The odor control composition includes (A) from 85 wt % to 99.5 wt % of an olefin-based polymer and (B) from 15 wt % to 0.5 wt % of an odor suppressant. The odor suppressant is a blend composed of (Bi) an ionomer, (Bii) particles of zinc oxide, and (Biii) particles of copper oxide. The composition has a methyl mercaptan odor suppression value of greater than 45% as measured in accordance with ASTM D5504-12. The terms "composition" and "odor control composition" may be used interchangeably.

A. Seal Layer

The present multilayer film includes a seal layer. A "seal layer" is a layer that (i) seals the multilayer film to itself, (ii) seals the multilayer film to a seal layer of another multilayer film, or (iii) seals the multilayer film to an article. Typically, the seal layer is the innermost layer of the multilayer film. When the multilayer film is assembled as part of a pouch or a bag, the seal layer is typically heat-sealed to an opposing seal layer of another multilayer film. Such heat-sealing typically occurs along a common peripheral edge of the opposing multilayer films.

Non-limiting examples of suitable polymeric material for the seal layer include ethylene-based polymer, propylene-based polymer, ethylene vinyl acetate (EVA), ethylene methacrylate (EMA), ethylene n-butyl acetate (EnBA), ethylene ethyl acrylate copolymer (EEA), polyolefin plastomer (POP), low density polyethylene (LDPE), linear low density polyethylene (LLDPE), metallocene linear low density polyethylene (mLLDPE), styrene-ethylene-propylene-styrene (SEPS) rubber, styrene-isoprene block copolymer (SIS) and any combination thereof.

In an embodiment, when the seal layer contains EVA, the EVA containing from 15 wt % to 24 wt % vinyl acetate based on total weight to the EVA. A non-limiting example of suitable EVA is ELVAX® 3165 available from DuPont.

In an embodiment, when the seal layer contains LLDPE, the LLDPE has a density from 0.88 g/cc to 0.902 g/cc.

B. Barrier Layer

The present multilayer film includes a barrier layer. A "barrier layer" is a layer that prevents gases, such as oxygen, and/or carbon dioxide, and/or odor molecules, such as $H_2S$ and mercaptans, from permeating to the outside of the multilayer film. The barrier layer is composed of a material having barrier properties such as a low gas transmission rate. Gas transmission rates include, but are not limited to, oxygen transmission rate, moisture vapor transmission rate, and carbon dioxide transmission rate. The barrier layer may or may not determine the overall permeability of the entire multilayer film.

In an embodiment, the multilayer film includes one or more barrier layers.

Non-limiting examples of material suitable for the barrier layer include ethylene/vinyl alcohol copolymer, polyvinylidene dichloride, vinylidene chloride copolymer, amorphous nylon, polyester, polyester copolymer, glycol-modified polyester (PETG), amorphous polyester copolymer, polyethylene terephthalate, amorphous polyethylene terephthalate, vinylidene chloride and methyl acrylate copolymer, vinylidene chloride and methyl methacrylate copolymer, polyamide, and combinations thereof.

Non-limiting examples of polyester copolymer include EASTAR™ PP001, EASTAR™ Copolyester AN001, EASTAR™ Copolyester AN011, EASTAR™ Copolyester CN005, EASTAR™ Copolyester 6763, and EASTAPAK™ Copolyester 9921, and combinations thereof, available from Eastman Chemical.

Non-limiting examples of other suitable barrier materials include polyethylene terephthalates, including Selar® available from DuPont.

A non-limiting example of PETG is EASTAR™ PETG 6763 available from Eastman Chemical.

C. Odor Control Layer

The present multilayer film includes an odor control layer. An "odor control layer" is a layer that absorbs odors and prevents odors from permeating to the outside of the multilayer film, the odor control layer being in a layer that is separate, or is otherwise distinct from, the barrier layer. The odor control layer thus provides the multilayer film further odor absorbing capacity in addition to the barrier layer. The odor control layer can be a discrete layer. Alternatively, the odor control layer can be a component of another layer (with exception to the barrier layer) as will be discussed in detail below.

In an embodiment, the odor control layer is a separate, discrete layer of the multilayer film. The odor control layer includes a composition (i.e. odor control composition) that includes (A) an olefin-based polymer and (B) an odor suppressant. The odor suppressant includes a blend of: (Bi) an ionomer, (Bii) particles of zinc oxide, and (Biii) particles of copper oxide.

Olefin-Based Polymer

The composition (odor control composition) of the odor control layer includes an olefin-based polymer. The olefin-based polymer can be a propylene-based polymer or an ethylene-based polymer. Non-limiting examples of propylene-based polymer include propylene copolymer, propylene homopolymer, and combinations thereof. In an embodiment, the propylene-based polymer is a propylene/$\alpha$-olefin copolymer. Non-limiting examples of suitable $\alpha$-olefins include $C_2$ and $C_4$-$C_{20}$ $\alpha$-olefins, or $C_4$-$C_{10}$ $\alpha$-olefins, or $C_4$-$C_8$ $\alpha$-olefins. Representative $\alpha$-olefins include ethylene, 1-butene, 1-pentene, 1-hexene, 1-heptene and 1-octene.

In an embodiment, the propylene/$\alpha$-olefin copolymer is a propylene/ethylene copolymer containing greater than 50 wt % units derived from propylene, or from 51 wt %, or 55 wt %, or 60 wt % to 70 wt %, or 80 wt %, or 90 wt %, or 95 wt %, or 99 wt % units derived from propylene, based on the weight of the propylene/ethylene copolymer. The propylene/ethylene copolymer contains a reciprocal amount of units derived from ethylene, or from less than 50 wt %, or 49 wt %, or 45 wt %, or 40 wt % to 30 wt %, or 20 wt %, or 10 wt %, or 5 wt %, or 1 wt % units derived from ethylene, based on the weight of the propylene/ethylene copolymer.

In an embodiment, the olefin-based polymer is an ethylene-based polymer. The ethylene-based polymer can be an ethylene homopolymer or an ethylene/$\alpha$-olefin copolymer.

In an embodiment, the ethylene-based polymer is an ethylene/$\alpha$-olefin copolymer. Non-limiting examples of suitable $\alpha$-olefins include $C_3$-$C_{20}$ $\alpha$-olefins, or $C_4$-$C_{10}$ $\alpha$-olefins, or $C_4$-$C_8$ $\alpha$-olefins. Representative $\alpha$-olefins include propylene, 1-butene, 1-pentene, 1-hexene, 1-heptene and 1-octene.

In an embodiment, the ethylene/$\alpha$-olefin copolymer is an LLDPE that is an ethylene/$C_4$-$C_8$ $\alpha$-olefin copolymer. The LLDPE has one, some, or all of the following properties:

(i) a density from 0.910 g/cc to 0.930 g/cc, or from 0.915 g/cc to 0.926 g/cc; and/or (ii) a melt index from 0.5 g/10 min, or 1.0 g/10 min, or 2.0 g/10 min to 3.0 g/10 min, or 4.0 g/10 min, or 5.0 g/10 min.

Non-limiting examples of a suitable LLDPE include DOWLEX™ 2247 G available from The Dow Chemical Company, and ELVAX® 3165 available from DuPont.

Odor Suppressant

The composition of the odor control layer includes an odor suppressant. The odor suppressant is composed of a (Bi) an ionomer, (Bii) particles of zinc oxide, and (Biii) particles of copper oxide.

(Bi) Ionomer

The present composition includes an ionomer. An "ionomer," as used herein, is an ion-containing polymer. An "ion" is an atom that has an electrical charge, either positive or negative. The ionomer has a majority weight percent (generally 85% to 90%) of repeating monomer units that are non-ionic (non-polar), and a minority weight percent (generally 10% to 15%) of repeating comonomer units that are ionic, or polar (i.e., positively-charged or negatively-charged). The positive charges of the ionic groups attract the negative charges of the ionic groups, creating ionic bonds. Ionomer resins exhibit what is known as "reversible cross-linking" behavior, i.e. when an ionomer is heated, the polymer chains have increased mobility, and the ionic bonds cannot stay intact because the positive charges and negative charges are pulled away from each other.

Non-limiting examples of the monomers and comonomers from which an ionomer is derived include a copolymer of at least one alpha-olefin and at least one ethylenically unsaturated carboxylic acid and/or anhydride. Non-limiting examples of suitable alpha-olefins include ethylene, propylene, 1-butene, 1-pentene, 1-hexene, 1-heptene, 1-octene, and 3-methylbutene. Non-limiting examples of suitable carboxylic acids and anhydrides include acrylic acid, methacrylic acid, ethacrylic acid, maleic acid, fumaric acid, and maleic anhydride.

In an embodiment, the ionomer is a copolymer of ethylene and methacrylic acid.

In an embodiment, the ionomer is a copolymer of ethylene and acrylic acid.

In an embodiment, the ionomer is a metal ionomer. A "metal ionomer," as used herein, refers to a copolymer based on a metal salt of a copolymer of an alpha-olefin and an ethylenically unsaturated carboxylic acid and/or anhydride. The metal ionomer may be fully or partially neutralized by a metal ion. Non-limiting examples of metals suitable for neutralizing an ionomer include the alkali metals, i.e., cations such as sodium, lithium, and potassium; alkaline earth metals, i.e., cations such as calcium, magnesium; and transition metals such as zinc. A non-limiting example of a metal ionomer is Surlyn® 8660, which is a sodium salt of an ethylene and methacrylic acid copolymer, available from Dow-DuPont.

In an embodiment, the metal ionomer is a zinc ionomer. The term "zinc ionomer," (or "ZnI/O") as used herein, refers to a copolymer based on a zinc salt of a copolymer of ethylene and a vinyl comonomer with carboxylic acid and/or anhydride. Non-limiting examples of suitable comonomers having vinyl comonomer with an acid group include methyl/methacrylic acid, vinyl acrylic acid, methacrylate, n-butyl acrylic acid, and acrylic acid.

Non-limiting examples of suitable zinc ionomers include zinc salt of ethylene/acrylic acid comonomer, zinc salt of ethylene/methyl-methacrylic acid copolymer, zinc salt of ethylene/vinyl acrylic acid copolymer, zinc salt of ethylene/methacrylate copolymer, zinc salt of ethylene/n-butyl acrylic acid copolymer, and any combination thereof.

In an embodiment, the zinc ionomer is a zinc salt of ethylene/acrylic acid copolymer. Non-limiting examples of suitable zinc ionomer include Surlyn® 9150, which is a zinc salt of an ethylene and methacrylic acid copolymer, available from Dow-DuPont.

B(ii) Particles of Zinc Oxide

The odor suppressant includes particles of zinc oxide (or "ZnO"). The ZnO particles have a D50 particle size from 100 nm to 3000 nm, a surface area from 1 $m^2/g$ to less than 10 $m^2/g$, and a porosity less than 0.020 $m^3/g$.

In an embodiment, the ZnO particles have one, some, or all of the following properties (i)-(iii) below:

(i) a particle size D50 from 100 nm, or 200 nm, or 300 nm, or 400 nm to 500 nm, or 600 nm, or 700 nm, or 800 nm, or 900 nm, or 1000 nm, or 2000 nm, or 3000 nm; and/or (ii) a surface area from 1 $m^2/g$, or 2 $m^2/g$, or 3 $m^2/g$, or 4 $m^2/g$ to 5 $m^2/g$, or 6 $m^2/g$, or 7 $m^2/g$, or 8 $m^2/g$, or 9 $m^2/g$; and/or (iii) a porosity from 0.005 $m^3/g$, or 0.006 $m^3/g$, or 0.008 $m^3/g$, or 0.010 $m^3/g$ to 0.012 $m^3/g$, or 0.013 $m^3/g$, or 0.015 $m^3/g$, or less than 0.020 $m^3/g$.

Non-limiting examples of suitable ZnO particles include 800HSA (Zinc Oxide, LLC), ZnO micropowder (US Research Nanomaterials), and Zoco102 (Zochem, Inc.).

(Biii) Particles of Copper Oxide

The odor suppressant also includes particles of copper oxide. The copper oxide can be either "$Cu_2O$" (copper I oxide) or "CuO" (copper II oxide), or a mix of both. The copper oxide particles have a D50 particle size from 100 nm to 3000 nm and a surface area from 1 $m^2/g$ to less than 10 $m^2/g$. Bounded by no particular theory, it is believed that the copper oxide particles contribute as a sulfur scavenger for hydrogen sulfide and mercaptans in particular.

In an embodiment, the copper oxide particles have a particle size D50 from 100 nm, or 200 nm, or 300 nm, or 400 nm, to 500 nm, or 600 nm, or 700 nm, or 800 nm, or 900 nm, or 1000 nm, or 2000 nm, or 3000 nm. Non-limiting examples of suitable copper oxide particles include $Cu_2O$ and CuO around 325 mesh available from Reade Advanced Materials.

Composition

The composition of the odor control layer includes (A) from 85 wt % to 99.5 wt % of the olefin-based polymer and (B) from 15 wt % to 0.5 wt % of the odor suppressant, based on total weight of the composition (hereafter, Composition 1). The odor suppressant is mixed, or otherwise blended, into the olefin-based polymer matrix, and is a blend of (Bi) an ionomer, (Bii) particles of zinc oxide, and (Biii) particles of copper oxide. The composition has an odor suppression value of greater than 45%. In an embodiment, the composition has an odor suppression value from 46%, or 49%, or 50% or 60% or 70% to 75%, or 80%, or 85%, or 90%.

The ZnI/O (Bi) is present in component (B) in an amount of 1 to 90 wt % based on the total weight of component (B). The ratio of ZnO to ZnI/O (hereafter "ZnO to ZnI/O ratio") is from 3:1 to 1:7 based on the total weight of the odor suppressant (B). The ZnO to ZnI/O ratio can be from 3:1, or 2:1, or 1:1 to 1:2, or 1:3, or 1:4, or 1:5, or 1:6, or 1:7. The particles of copper oxide (Biii) are present in component (B) in an amount of from 0.01 to 30 wt % by the total weight of component (B). The particles of copper oxide can be copper (I) oxide ($Cu_2O$), copper (II) oxide (CuO), or a mix of both. The weight percent ratio between the ionomer (Bi) the zinc oxide (Bii) and the copper oxide (Biii) is 150:100:1 to 2.9:2.5:1 based on the total weight of the odor suppressant (B).

In an embodiment, the weight percent ratio between the ionomer (Bi), the zinc oxide (Bii), and the copper oxide (Biii) is from 100:75:1 to 3:2.5:1 based on the total weight of the odor suppressant (B).

In an embodiment, the composition includes from 85 wt %, or 90 wt % to 95 wt %, or 97 wt %, or 99 wt %, or 99.4 wt %, or 99.5 wt % component (A) that is an ethylene-based polymer. The composition includes a reciprocal amount of component (B), or from 15 wt %, or 10 wt % to 5 wt %, or 3 wt %, 1 wt %, or 0.6 wt %, or 0.5 wt % odor suppressant wherein Zn I/O to ZnO to $Cu_2O$ ratio is 150:100:1 to 2.9:2.5:1 (hereafter Composition 2).

The composition (i.e. Composition 1 and/or Composition 2) has an odor suppression value from 46%, or 50%, or 60%, or 70% to 75%, or 80%, or 85%, or 90%.

While the combination of ZnO and ionomer improve OSV for methyl mercaptan, the addition of copper oxide, and in particular $Cu_2O$, has been observed to further improve overall OSV. In fact, Applicant surprisingly discovered that the addition of from 0.01 wt % to 0.1 wt % of $Cu_2O$ to a ZnO/ionomer odor suppressing composition (based on the total weight of odor suppressant composition (B), for example) can more than double the OSV performance compared to ZnO/ionomer odor suppressing compositions that lack the copper oxide particles.

D. Blend

Components (A) and (B) are mixed, or otherwise blended, together to form the present composition so that the particles of zinc oxide and the particles of copper oxide are (i) dispersed within the olefin-based polymer (A) and/or (i) dispersed within the ionomer (Bi).

In an embodiment, the present composition is produced as an odor control masterbatch wherein component (B) is formed by dispersing the zinc oxide particles (Bii) and the copper oxide particles (Biii) into the ionomer (Bi). The dispersing may be accomplished by physical mixing and/or melt blending of components (Bi), (Bii), and (Biii) in order to uniformly disperse the particles (zinc oxide and copper oxide) throughout the ionomer. The resultant component (B) is subsequently mixed, or otherwise blended, with the olefin-based polymer, component (A). The mixing of component (B) and component (A) may be accomplished by physical mixing and/or melt blending (hereafter odor control masterbatch 1).

In an embodiment, the present composition is produced as an odor control masterbatch by dispersing the zinc oxide particles (Bii) into the ionomer (Bi). The dispersing may be accomplished by physical mixing and/or melt blending of components (Bi) and (Bii) in order to uniformly disperse the zinc particles throughout the ionomer (Bi) ("Bi-Bii blend"). The Bi-Bii blend and the copper oxide particles are subsequently added to the olefin-based polymer composition (A) by physical mixing and/or melt blending to form the present composition of a homogeneous blend of olefin-based polymer (A), ionomer (Bi), zinc oxide particles (Bii), and copper oxide particles (Biii) (hereafter odor control masterbatch 2).

In an embodiment, the present composition is produced as an odor control masterbatch by mixing the ionomer (Bi), the zinc oxide particles (Bii), the copper oxide particles (Biii) and the olefin-based polymer (A). The mixing may be accomplished by physical mixing and/or melt blending of components (A), (Bi), (Bii), and (Biii) in order to uniformly disperse the ionomer (Bi), the zinc oxide particles (Bii), and the copper oxide particles (Biii) throughout the olefin-based polymer (A) (hereafter odor control masterbatch 3).

In an embodiment, the present composition is produced as an odor control masterbatch by mixing the ionomer (Bi), the zinc oxide particles (Bii), and the olefin-based polymer (A). The mixing may be accomplished by physical mixing and/or melt blending of components (Bi), (Bii), and (A) in order to uniformly disperse (Bi) and (Bii) throughout (A) (hereafter, A-Bi-Bii blend). Copper oxide particles (Biii) are mixed with component (A). The mixing may be accomplished by physically mixing and/or melt blending in order to uniformly disperse the copper oxide particles (Biii) into (A) (hereafter, A-Biii blend). The A-Bi-Bii blend is then mixed with the A-Biii blend. The mixing may be accomplished by physical mixing and/or melt blending to form a homogeneous composition composed of olefin-based polymer (A), ionomer (Bi), zinc oxide particles (Bii), and copper oxide particles (Biii) (hereafter, odor control masterbatch 4).

In an embodiment, the odor control masterbatch (i.e., any of odor control masterbatch 1, 2, 3, or 4) includes from 20 wt % to 30 wt % ionomer, from 20 wt % to 30 wt % particles of zinc oxide, from 5 wt % to 15 wt % particles of copper oxide, and from 30 wt % to 60 wt % LLDPE, with the aggregate of the components amounting to 100 wt % odor control composition. The masterbatch is then incorporated at 10 wt % into the odor control layer of the multilayer film, providing 6 wt % of the composition to the odor control layer. The odor control layer is a maximum of 40 vol % of the total volume of the multilayer film, and thus the composition has a maximum of 2.4 wt % of the entire weight of the multilayer film.

E. Skin Layer

In an embodiment, the multilayer film includes a skin layer. A "skin layer" is the outermost layer of the multilayer film.

Non-limiting examples of suitable polymeric material for the skin layer include ethylene-based polymer, propylene-based polymer, ethylene vinyl acetate (EVA), ethylene methacrylate (EMA), ethylene n-butyl acetate (EnBA), ethylene ethyl acrylate copolymer (EEA), polyolefin plastomer (POP), low density polyethylene (LDPE), linear low density polyethylene (LLDPE), metallocene linear low density polyethylene (mLLDPE), styrene-ethylene-propylene-styrene (SEPS) rubber, styrene-isoprene block copolymer (SIS) and any combination thereof.

In an embodiment, when the skin layer contains EVA, the EVA contains from 15 wt % to 24 wt % vinyl acetate based on the total weight of the EVA. A non-limiting example of suitable EVA is ELVAX® 3165 available from DuPont.

In an embodiment, when the skin layer contains LLDPE, the LLDPE having a density from 0.88 g/cc to 0.902 g/cc.

In an embodiment, the skin layer may be composed of the same material composition as the seal layer.

F. Tie Layer

In an embodiment, the multilayer film includes at least one tie layer. A "tie layer" is a layer composed of a tie material, the tie material/tie layer adhering one layer of the multilayer film to another layer of the multilayer film. The tie layer may be, for example, between the seal layer and the barrier layer, and/or between the barrier layer and the skin layer.

Non-limiting examples of material suitable for the tie layer include ethylene vinyl acetate (EVA), ethylene methacrylate EMA, ethylene butyl acrylate (EBA), ethylene acrylic acid (EAA), maleic anhydride-grafted EVA (EVA-g-MAH), EMA-g-MAH, EBA-g-MAH, MAH-grafted polyethylene, and combinations thereof.

A non-limiting example of a suitable tie material is EVATANE® 24-03 available Arkema, an EVA.

Non-limiting examples of MAH-grafted polyethylene include Engage-g-MAH (e.g. AMPLIFY™ TY by the Dow Chemical Company).

In an embodiment, the odor control layer may be present in at least one of the tie layer, and the skin layer. In an embodiment, the odor control layer can be in both the tie layer and the skin layer. In other words, the odor control composition may be incorporated into the skin layer, and/or the tie layer.

G. Core Layer

In an embodiment, the multilayer film includes a core layer. A "core layer" is a layer that can be any inner layer (i.e. non-skin layer and non-seal layer) of the multilayer film. The core layer provides the multilayer film with desired physical properties, including but not limited to strength, optics, and permeability. However, it is desirable that the core provide at least some barrier property.

In an embodiment, the odor control composition can be incorporated into the core layer.

Multilayer Film

The multilayer film includes at least three layers: a seal layer, a barrier layer, and an odor control layer, as disclosed herein. The multilayer film may include three, four, five, six, seven, eight, nine, ten, or more layers. The multilayer film has a thickness from 30 µm, or 40 µm, or 45 µm, or 50 µm, or 75 µm, to 100 µm, or 125 µm, or 150 µm.

In an embodiment, the multilayer film has a thickness from 45 µm or 50 µm to 75 µm, or 100 µm.

In an embodiment, the multilayer film includes three layers: the seal layer as the innermost layer, the barrier layer as the middle layer, and the odor control layer as the outermost layer, or the skin layer. The skin layer may be (i) a blend of the odor control composition and skin layer material or (ii) composed solely of the odor control composition.

In an embodiment, the multilayer film includes four layers (from innermost to outermost): a seal layer as the innermost layer, a barrier layer, a tie layer with the odor control composition, and a skin layer as the outermost layer. The tie layer is a blend of (i) a tie material, and (ii) the odor control composition.

In an embodiment, the multilayer film includes five layers (from innermost to outermost): a seal layer, a first tie layer, a barrier layer, a second tie layer, and an odor control layer. The seal layer is the innermost layer of the multilayer film. The barrier layer is between the seal layer and the odor control layer. The odor control layer is in the skin layer. The skin layer may be (i) a blend of the odor control composition and skin material or (ii) composed solely of the odor control composition.

In an embodiment, the multilayer film includes six layers (from innermost to outermost): a seal layer as the innermost layer, a first tie layer, a barrier layer, a second tie layer, an odor control layer, and a skin layer. In a further embodiment, the second tie layer is a blend of (i) a tie material and (ii) the odor control composition.

In an embodiment, the odor control layer is a skin layer and is the outermost layer of the multilayer film. The skin layer may be (i) a blend of the odor control composition and skin layer material or (ii) composed solely of the odor control composition. When the odor control layer is the skin layer, the multilayer film may include a tie material for adhesion to the barrier layer, or to another layer.

In an embodiment, the multilayer film includes a first tie layer between the seal layer and the barrier layer, for adhesion of the seal layer to the barrier layer. The multilayer film also includes a second tie layer between the barrier layer and the skin layer, for adhesion of the barrier layer to the skin layer. The skin layer may be (i) a blend of the odor control composition and skin layer material or (ii) composed solely of the odor control composition. The second tie layer may also include the odor control composition.

In an embodiment, the seal layer is from 10 vol %, or 15 vol %, or 20 vol %, or 25 vol % to 30 vol %, or 35 vol %, or 40 vol %, or 45 vol % of the multilayer film, based on total volume of the multilayer film.

In an embodiment, the barrier layer is from 4 vol % to 15 vol %, or from 5 vol % to 12 vol %, or from 6 vol % to 8 vol % of the multilayer film, based on total volume of the multilayer film.

In an embodiment, the odor control layer is from 5 vol % to 40 vol %, or from 8 vol % to 20 vol % of the multilayer film, based on total volume of the multilayer film.

In an embodiment, each tie layer is from 4 vol % to 15 vol %, or from 5 vol % to 12 vol %, or from 5 vol % to 8 vol % of the multilayer film, based on total volume of the multilayer film.

In an embodiment, the skin layer is from 10 vol %, or 15 vol %, or 20 vol %, or 25 vol % to 30 vol %, or 35 vol %, or 40 vol %, or 45 vol % of the multilayer film, based on total volume of the multilayer film.

In an embodiment, the multilayer film may also include a core layer as described herein.

In an embodiment, the multilayer film is a coextruded film. Non-limiting examples of a coextruded film include meltblown film and cast film.

In an embodiment, the multilayer film is a laminated film. For a laminated film, the multilayer film can include thin adhesives as the tie layer and/or be an extrusion-laminated film.

In an embodiment, the multilayer film includes five layers (from innermost to outermost): a seal layer as the innermost layer, a first tie layer, a barrier layer, a second tie layer, and an odor control layer that is the outermost layer, or skin layer. The seal layer contains ELVAX® 3165 and is 37 vol % of the total volume of the multilayer film. The first tie layer contains BYNEL® 3861 and is 8 vol % of the total volume of the multilayer film. The barrier layer contains EASTAR™ PP001 and is 10 vol % of the total volume of the multilayer film. The second tie layer contains BYNEL® 3861 and is 8 vol % of the total volume of the multilayer film. The odor control layer is a blend of (i) ELVAX® 3165 and (ii) the odor control composition. The odor control layer is 37 vol % of the total volume of the multilayer film (hereafter film1).

In an embodiment, the second tie layer of film 1 includes a blend of (i) tie material and (ii) the odor control composition.

In an embodiment, film1 contains the odor control composition in the odor control layer, with the odor control layer including 90 wt % ELVAX® 3165 and 10% of the odor control composition including of (i) 4 wt % DOWLEX™ 2247G+(ii) 2.5 wt % ZnO (500 μm)+(iii) 2.5 wt % Surlyn® 9150+(iv) 1 wt % $Cu_2O$.

Bag

The present disclosure provides a bag. In an embodiment, an ostomy bag is provided and includes a first multilayer film and a second multilayer film. Each multilayer film is composed of a seal layer, a barrier layer, and an odor control layer. The odor control layer includes a composition, with the composition including: (A) from 85 wt % to 99.5 wt % of at least one olefin-based polymer; and (B) from 15 wt % to 0.5 wt % of an odor suppressant comprising a blend of: (i) an ionomer; (ii) particles of zinc oxide; and (iii) particles of copper oxide. The first multilayer film and the second multilayer film can be any multilayer film as previously disclosed herein.

The first multilayer film and the second multilayer film are arranged such that the seal layers oppose each other, and the second multilayer film is superimposed on the first multilayer film to form a common peripheral edge. The first multilayer film and the second multilayer film are sealed along the common peripheral edge.

The first multilayer film and the second multilayer film of the bag may be any embodiment of the multilayer films previously disclosed herein. The first multilayer film and the second multilayer film may be composed of the same materials, or different materials.

The first multilayer film includes a first opening, for receiving a stoma and fluids from a human body into the bag.

The ostomy bag includes a ring. The ring is adhered to the first opening. The ring is for attachment to the human body. The ring typically includes an adhesive material on a contact surface, enabling the ostomy bag to securely and resealably attached to the skin of a person wearing the ostomy bag.

In an embodiment, the peripheral seal may extend around the entire bag.

In an embodiment, the peripheral seal extends along a portion of the common peripheral edge of the ostomy bag, leaving open an unsealed portion. A second opening, for removing the stoma and fluids from the bag, is formed from the unsealed portion of peripheral seal.

In an embodiment, the composition has a methyl mercaptan odor suppression value of greater than 45% as measured in accordance with ASTM D5504-12.

By way of example, and not limitation, some embodiments of the present disclosure will now be described in detail in the following Examples.

EXAMPLES

Materials used in the examples are provided in Table 1 below.

TABLE 1

| Material/Description | Properties | Source |
| --- | --- | --- |
| Ethylene/octene (LLDPE 1) | 0.9 melt flow rate (I2) (g/10 min) 0.923 g/cc | The Dow Chemical Company |
| ZnO 800HSA Zinc Oxide micro-powder (ZnO-1) | ZnO D50 particle size 3000 nm; density = 5.61 g/cc; Porosity 0.0131 g/m³, surface area 4.46 m²/g | Zinc Oxide, LLC |
| Zinc Oxide micro-powder (ZnO-2) | ZnO D50 particle size 500 nm; density = 5.61 g/cc; Porosity 0.008 m³/g, surface area 3.36 m²/g | 500 nm (US Research Nanomaterials) |
| Zoco102 Zinc Oxide micro-powder (ZnO-3) | ZnO D50 particle size 200 nm; density = 5.61 g/cc; Porosity 0.012 m³/g, surface area 4.4 m²/g | Zochem, Inc. |
| Ampacet 110069 White PE MB Titanium dioxide (TiO$_2$) Masterbatch | 70 wt % TiO$_2$ in Carrier Resin LLDPE (MI 2.3, d- 0.917 g/cc) Masterbatch Specific gravity: 2.03 | Ampacet Corporation |
| Surlyn ® 9150 (Zinc Ionomer) | Ethylene/Methacrylic Acid Copolymer, zinc cation Density 0.970 g/cc, melt flow 4.5 g/10 min | Dow-DuPont |
| Cu$_2$O | 325 mesh | Reade Advanced Materials |
| EVATANE ® 24-03 | Ethyl Vinyl Acetate 3 melt index (I$_2$) (g/10 min); Density 0.94 g/cc; Tm = 80° C.; 24 wt % vinyl acetate | Arkema |
| BYNEL ® 3861 | 2 melt index (I$_2$) (g/10 min); Density 0.95 g/cc; Tm = 80° C.; EVA-gMAH 24 wt % vinyl acetate | DuPont |
| EASTAR™ PP001 | Copolyester copolymer Density 1.27 g/cc; Shore A hardness 83 Shore D hardness 73 | Eastman Chemical |

1. Films

Master batch processing. Two master batches were prepared to ease feeding the odor suppressing compositions into a subsequent film line. The master batches were prepared on a Coperion ZSK 26 twin screw extruder using a general purpose screw. The residence time of material was controlled by the screw design, feed rate of 20 lbs/hr, and a screw speed of 300 revolutions per minute (RPM). No oil was injected. There was no side arm feeder. No vacuum was pulled. The compounded material was sent through a water bath before being cut by a strand cut pelletizer. After collection the pelletized materials were N$_2$ purged, then sealed in an aluminum bag.

The composition of the first master batch (MB1) was 50 wt % LLDPE 1, 25 wt % ZnO, and 25 wt % Surlyn 9150. The composition of the second master batch (MB2) was 90 wt % LLDPE 1 and 10 wt % Cu$_2$O. Examples and counter example formulations were generated using the appropriate amount of pure LLDPE 1, MB1 and MB2 to achieve the target weight % of each composition listed.

TABLE 2

| Blown film line process parameters | | | |
| --- | --- | --- | --- |
| Parameter | Units | Films without TiO$_2$ MB | Films containing TiO$_2$ MB |
| Takeoff | m/min | 15 | 15 |
| Layflat | cm | 23.5 | 23.5 |
| Frostline | cm | 14 | 14 |
| B.U.R | ratio | 2.5 | 2.5 |
| Die gap | mm | 2.0 | 2.0 |
| Melt temperature - Ext. A | ° C. | 218 | 218 |
| Melt temperature - Ext. B | ° C. | 226 | 226 |
| Melt temperature - Ext. C | ° C. | 215 | 215 |
| RPM - Ext. A | rpm | 51 | 51 |
| RPM - Ext. B | rpm | 50 | 50 |
| RPM - Ext. C | rpm | 32 | 32 |
| Total Output | kg/hr | 8.8 | 8.8 |
| Film Total Thickness | mm | 0.023 | 0.056 |

2. Odor Suppression

The compositions of comparative samples (CS) and inventive examples (IE) are shown in Table 3.

The odor suppression values (OSV) for are provided in Table 3 below. Concentrations were measured using the reference sample (CS 1) as the calibration standard after two days, concentrations in the reference sample might change after two days, so the concentrations in the samples should be considered as the relative change to the reference sample.

TABLE 3

| Odor Suppression Values and Blown Film Properties OSV of Methyl Mercaptan | | |
| --- | --- | --- |
| Sample | Components | Methyl Mercaptan OSV (%) |
| CS 1 | 99% LLDPE 1 + 1% TiO$_2$ MB | 12 |
| CS 2 | 97.5% LLDPE 1 + 2.5% TiO$_2$ MB | 2 |

TABLE 3-continued

Odor Suppression Values and Blown Film Properties
OSV of Methyl Mercaptan

| Sample | Components | Methyl Mercaptan OSV (%) |
|---|---|---|
| CS 3 | 99% LLDPE 1 + 0.5 wt % ZnO + 0.5 wt % Zinc Ionomer | 28 |
| CS 4 | 97.5% LLDPE 1 + 1.25 wt % ZnO + 1.25 wt % Zinc Ionomer | 44 |
| IE 1 | 97.4% LLDPE 1 + 1.25 wt % ZnO + 1.25 wt % Zinc Ionomer + 0.1% $Cu_2O$ | 80 |
| IE 2 | 98.9% LLDPE 1 + 0.5 wt % ZnO + 0.5 wt % Zinc Ionomer + 0.1% $Cu_2O$ | 64 |
| IE 3 | 99.4% LLDPE 1 + 0.25 wt % ZnO + 0.25 wt % Zinc Ionomer + 0.1% $Cu_2O$ | 49 |

Zinc ionomer used in Table 3 is Surlyn 9150
*$TiO_2$ MB—titanium dioxide masterbatch 70 wt % $TiO_2$ powder in 30 wt % LLDPE carrier, added for white color In Table 3, component amounts for each sample yield 100 wt % total sample composition. It can readily be observed that the ZnO/zinc ionomer combination is effective in improving OSV as compared to a composition that lacks any odor suppressing technology by comparing the OSV for CS 3 (28%) to the OSVs for CS 1 & 2 (12% and 2% respectively). However, it is surprising to see that although $Cu_2O$ is added at very low loadings as part of the present odor suppressant (i.e., at <10% of the combination of ZnO, zinc ionomer, and $Cu_2O$ in IE2), it can further improve the OSV to 64% as compared to CS 3 OSV of 28%, (i.e., the sample with zinc ionomer and ZnO, and without $Cu_2O$ present). The addition of $Cu_2O$ unexpectedly allows for a reduction in ZnO/zinc ionomer concentrations by 50% in the composition while maintaining an OSV that is almost 50% higher than the ZnO/zinc ionomer combination that does not have $Cu_2O$ present, as can be observed by comparing the OSV for IE3 (49%) to the OSV of CS3 (28%). It is further observed that the ZnO/zinc ionomer combination still exhibits a significant influence on OSV in that higher loadings of these materials in combination with 0.1 wt % $Cu_2O$ exhibits the highest OSV of the inventive examples IE1 (80%) and IE2 (64%) shown in Table 3.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A multilayer film comprising:
(A) a seal layer;
(B) a barrier layer; and
(C) an odor control layer, comprising a composition, the composition comprising:
(A) from 85 wt % to 99.5 wt % of at least one olefin-based polymer;
(B) from 15 wt % to 0.5 wt % of an odor suppressant comprising a blend of:
(i) an ionomer;
(ii) particles of zinc oxide; and
(iii) particles of copper oxide;
wherein the composition has a methyl mercaptan odor suppression value of greater than 45% as measured in accordance with ASTM D5504-12.

2. The multilayer film of claim 1, wherein the barrier layer is between the seal layer and the odor control layer.

3. The multilayer film of claim 2, wherein the seal layer is an innermost layer.

4. The multilayer film of claim 3, wherein the odor control layer comprises a tie material.

5. The multilayer film of claim 3, wherein the seal layer is composed of a polymeric material selected from the group consisting of an ethylene-based polymer, a propylene-based polymer, ethylene vinyl acetate (EVA), ethylene methyl acrylate (EMA), ethylene n-butyl acetate (EnBA), ethylene ethyl acrylate copolymer (EEA), polyolefin plastomer (POP), low density polyethylene (LDPE), linear low density polyethylene (LLDPE), metallocene linear low density polyethylene (mLLDPE), styrene-ethylene-propylene-styrene (SEPS) rubber, styrene-isoprene block copolymer (SIS) and combinations thereof.

6. The multilayer film of claim 1, wherein the barrier layer is composed of a polymeric material selected from the group consisting of ethylene/vinyl alcohol copolymer, polyvinylidene dichloride, vinylidene chloride copolymer, amorphous nylon, polyester, polyester copolymer, glycol-modified polyester (PETG), amorphous polyester copolymer, polyethylene terephthalate, amorphous polyethylene terephthalate, vinylidene chloride and methyl acrylate copolymer, vinylidene chloride and methyl methacrylate copolymer, polyamide, and combinations thereof.

7. The multilayer film of claim 1, wherein the olefin-based polymer in the odor control layer is an ethylene-based polymer.

8. The multilayer film of claim 2 comprising a tie layer between the seal layer and the barrier layer.

9. The multilayer film of claim 1, further comprising a skin layer.

10. The multilayer film of claim 1, wherein the odor control layer is a skin layer.

11. The multilayer film of claim 1, wherein the ionomer comprises an ethylene/methacrylic acid copolymer.

12. The multilayer film of claim 1, wherein the ionomer is a zinc ionomer.

13. The multilayer film of claim 1, wherein the particles of copper oxide are selected from the group consisting of (i) copper (I) oxide ($Cu_2O$), (ii) copper (II) oxide (CuO), and (iii) combinations thereof.

14. The multilayer film of claim 12, wherein the weight percent ratio between the zinc ionomer (Bi), the zinc oxide (Bii), and the copper oxide (Biii) is from 150:100:1 to 2.9:2.5:1.

15. An ostomy bag comprising:
a first multilayer film and a second multilayer film, wherein each multilayer film comprises:
(A) a seal layer;
(B) a barrier layer; and
(C) an odor control layer, comprising a composition, the composition comprising:
(A) from 85 wt % to 99.5 wt % of an olefin-based polymer;
(B) from 15 wt % to 0.5 wt % of an odor suppressant comprising a blend of:
(i) an ionomer;
(ii) particles of zinc oxide; and
(iii) particles of copper oxide;
wherein the composition has a methyl mercaptan odor suppression value of greater than 45% as measured in accordance with ASTM D5504-12;
the first multilayer film and the second multilayer film arranged such that the seal layers oppose each other and the second multilayer film is superimposed on the first multilayer film to form a common peripheral edge;

the first multilayer film and the second multilayer film sealed along the common peripheral edge;
the first multilayer film comprising a first opening; and
a ring adhered to the first opening.

* * * * *